United States Patent [19]

Cage et al.

[11] Patent Number: 5,011,517
[45] Date of Patent: Apr. 30, 1991

[54] SAMPLER FOR CHEMICAL VAPORS

[75] Inventors: Brian R. Cage, Shawnee, Kans.; Arbor D. Drinkwine, Kansas City, Mo.

[73] Assignee: Midwest Research Institute, Kansas City, Mo.

[21] Appl. No.: 478,523

[22] Filed: Feb. 12, 1990

[51] Int. Cl.$^5$ .............................................. B01D 47/00
[52] U.S. Cl. ........................................ 55/92; 55/235; 55/270; 73/863.11; 73/863.12; 73/863.21
[58] Field of Search ................... 55/92, 222, 235-238, 55/270; 73/863.11, 863.12, 863.21

[56] References Cited

U.S. PATENT DOCUMENTS

| | | | |
|---|---|---|---|
| 901,010 | 10/1908 | Jacobs | 55/222 |
| 2,987,921 | 6/1961 | Kraftson | 73/863.12 |
| 3,324,632 | 6/1967 | Berneike et al. | 55/236 |
| 4,479,379 | 10/1984 | Tarcy | 55/270 |

Primary Examiner—Bernard Nozick
Attorney, Agent, or Firm—Kokjer, Kircher, Bradley, Wharton, Bowman & Johnson

[57] ABSTRACT

An instrument for removing chemical vapors from air and concentrating the chemical vapors in a liquid scrubbing medium has been invented. A cylindrical receptacle receives a preselected amount of scrubbing liquid. Air is pulled tangentially into the cylinder through an inlet slit and swirls toward the cylinder top, carrying the liquid with it so that the cylinder wall is coated with the liquid. At the end of a sampling cycle, the air flow is shut off and the liquid is allowed to settle before being drained off for analysis. A cleaning cycle between sampling cycles is possible, during which the cylinder can be heated by an electrical heater cable.

5 Claims, 1 Drawing Sheet

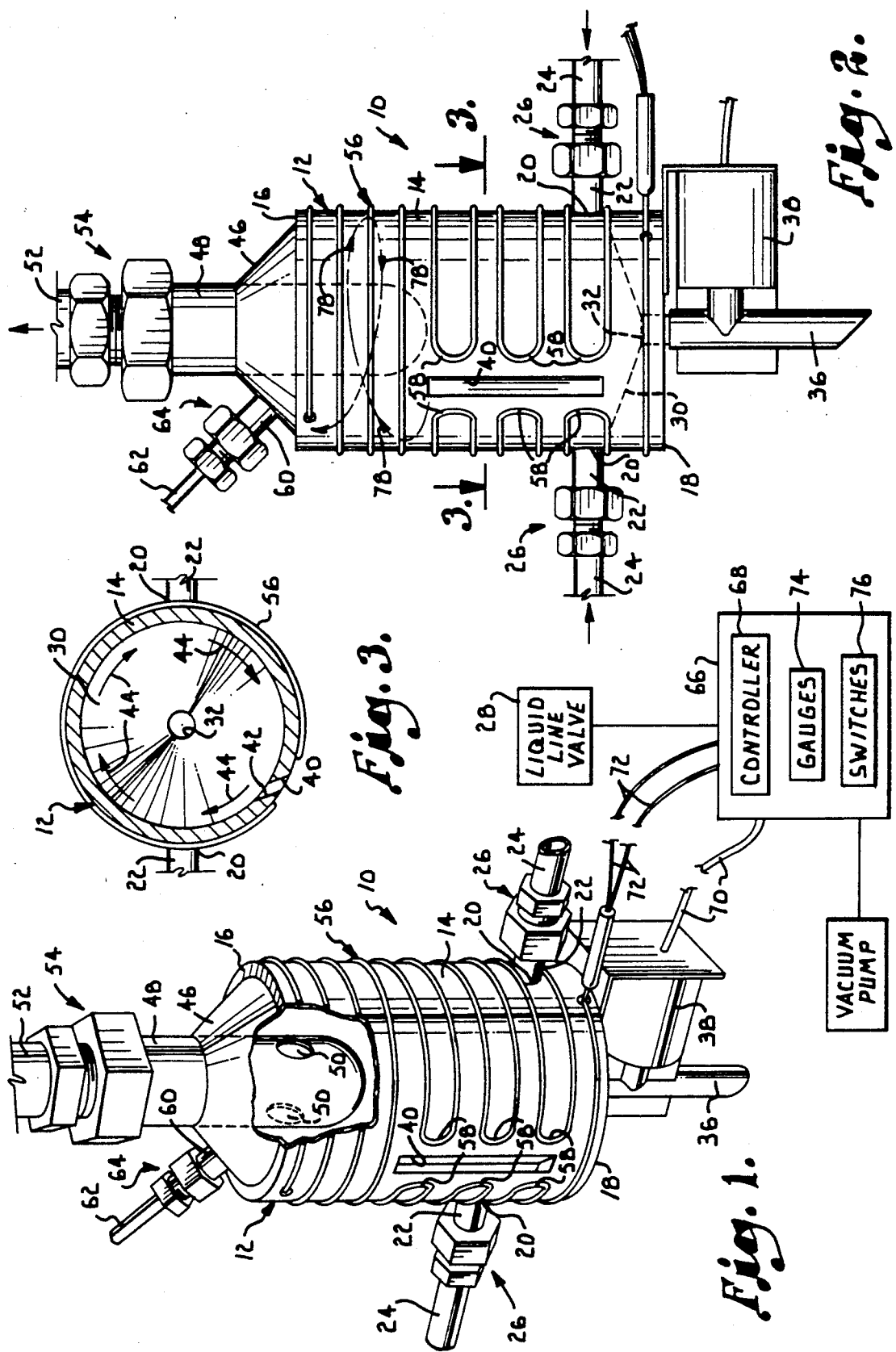

SAMPLER FOR CHEMICAL VAPORS

BACKGROUND AND SUMMARY OF THE INVENTION

This invention relates generally to the extraction of chemical vapors from air and more particularly to an improved method and apparatus for extracting chemical vapors and concentrating them in a liquid medium for analysis.

The invention was developed using explosives vapor as a model compound. Following is a description of the application of the chemical vapor sampler using explosives as a typical example. Utility for sampling other chemicals is further provided in the detailed description of the invention as well as the claims.

Hidden bombs, weapons and other concealed explosive devices can be detected by sensing the explosive vapors emitted from the device. It is generally recognized that there are at least three different applications for such a detection system, namely, the processing of people and items such as baggage or mail, the searching of areas by a portable system intended to locate a hidden store of explosives, and the continuous monitoring of an area to detect when an explosive device enters the area. For example, people and luggage can be processed as they enter transportation terminals or other buildings, including post offices, courthouses and auditoriums. Buildings can be searched for explosives if a bomb threat is received or when there is reason to suspect terrorist or sabotage activity. Airports, post offices, courthouses and other buildings that are common targets for terrorist activity can be monitored continuously to determine if an explosive device is brought into the building.

It is also generally recognized that an explosives vapor detection system which meets the varied requirements of these different applications should have three different components. Such a three component system requires a sampler which extracts sample air and concentrates the explosives vapor it contains, an analyzer which can evaluate the sample for the presence of explosives vapor, and a calibration module which periodically checks the performance of the system.

The present invention is directed to an improved process for extracting air samples and concentrating any chemical vapors the samples contain, for example explosives, and also to an improved apparatus for carrying out the process. The device of the present invention is especially well suited for use in a continuous monitoring application such as the monitoring of a transportation terminal. More specifically, the device is primarily intended to be installed in the ventilating ducts of a building to sample the air that is pulled through the duct work.

It is a particular feature of the invention that extremely low vapor concentrations can be collected so that the presence of chemicals can be detected with confidence and reliability. In this respect, it is noteworthy that the device functions on a batch type operating principle by which the chemical vapor contained in the air that is extracted is scrubbed by a minimal quantity of scrubbing liquid, thereby concentrating the vapor sufficiently that even minute amounts of chemical are detectable.

It is another important feature of the invention that the device has a relatively short operating cycle (typically, about 15 minutes) so that, for example, the entry of an explosive device into the monitored area is detected quickly enough that appropriate action can be taken.

It is still another feature of the invention that the device can operate either semi-automatically or under the control of a human operator.

Other and further features of the invention, including novel features of novelty appurtenant thereto, will be discussed in the course of the following description.

DESCRIPTION OF THE DRAWINGS

In the accompanying drawings which form a part of the specification and are to be read in conjunction therewith and in which like reference numerals are used to indicate like parts in the various views:

FIG. 1 is a fragmentary perspective view of a chemical vapor sampling device constructed according to a preferred embodiment of the present invention, with a portion broken away for purposes of illustration and the control system of the device shown diagrammatically;

FIG. 2 is a fragmentary front elevational view of the sampling device; and

FIG. 3 is a fragmentary sectional view taken generally along line 3—3 of FIG. 2 in the direction of the arrows.

DETAILED DESCRIPTION OF THE INVENTION

Referring now to the drawings in detail, numeral 10 generally designates a chemical vapor sampling device which functions to extract samples of the ambient air and concentrate any chemical vapor that is contained in the air for delivery to a suitable analyzing system. The sampling device 10 includes a hollow receptacle 12 which has a cylindrical wall 14 and top and bottom ends 16 and 18, respectively. Slightly above the bottom end 18 of the receptacle, the wall 14 is provided with diametrically opposed inlet ports 20 through which a suitable scrubbing liquid such as water is introduced into the receptacle. Extending to each port 20 is an inlet tube 22. Liquid delivery lines 24 connect with the tubes 22 by means of suitable fittings 26. The liquid lines 24 are supplied by a suitable source of water or other scrubbing liquid through a valve which is shown diagrammatically in FIG. 1 and identified by numeral 28.

Located inside of the receptacle 12 adjacent to its bottom end 18 is a funnel 30 (see FIG. 2). A drain port 32 is provided at the bottom of the funnel 30, and a short drain tube 34 extends downwardly from the drain port 32. Fitted over and connected with the drain tube 34 is a larger drain line 36 which is controlled by a solenoid pinch valve 38. The valve 38 opens and closes the drain line in a manner that will be described more fully.

The ambient air is able to enter the receptacle 12 through a vertically oriented inlet slit 40 formed in the cylinder wall 14. The bottom of the inlet slit 40 is located near the level of the liquid inlet ports 20, and the inlet slit extends upwardly through a major portion of the receptacle height. A beveled edge 42 is formed integral to the wall of the receptacle 12 and comprises the inlet slit 40 in order to direct the incoming air tangentially around the inside surface of the wall 14, as indicated by the directional arrows 44 in FIG. 3.

A truncated cone 46 is mounted on the top end 16 of receptacle 12. A vacuum tube 48 extends through the center of the cone 46 and into the interior of the receptacle 12. The tube 48 has a rounded end, and a pair of diametrically opposed vacuum ports 50 are formed in its opposite sides at a location within and near the top end of the receptacle. The tube 48 connects with a vacuum line 52 by means of a suitable fitting 54. A vacuum pump indicated diagrammatically in FIG. 1 and identified by numeral 55 connects with the vacuum line 52 and operates to apply a vacuum to the interior of the receptacle 12, as will be explained more fully.

The receptacle 12 is provided with an electrical heater cable which is generally identified by numeral 56 and which is an electrically resistive heater. The heater cable 56 is wrapped around the outside of the cylindrical wall 14. Above and below the inlet slit 40, the heater cable extends circumferentially around the wall 14. However, in the area occupied by the slit 40, the cable is provided with switchback loops which are indicated at 58 and which are arranged to apply heat relatively uniformly to the receptacle wall 14 without interfering with the inlet slit 40. The temperature to which the receptacle 12 is heated by the heater cable 56 is controlled by a suitable thermostat (the sensing probe of which is embedded in the wall 14).

The cone 46 is provided with a pressure sensor port which connects with tube 60. The tube 60 is in turn connected with a pressure sensing line 62 by a suitable fitting 64.

With reference to FIG. 1, a control console 66 is provided to permit either semi-automatic or manual control of the sampling device 10. The console 66 includes a programmable controller 68 which may be programmed to suitably control the valve 28, the vacuum pump 55, the solenoid pinch valve 38 and other components of the system. Wiring 70 extends from the console 66 to the solenoid valve 38, and additional lead wiring 72 extends from the console 66 to the heater cable 56. The console 66 also includes gauges which are identified collectively at 74 and which may provide readouts as to the air pressure, air flow rate, temperature and other operating parameters. The console 66 is also equipped with a bank of function switches 76 which control the various functions of the device. For example, the switches 76 may control functions such as the on/off condition of the system, the sample cycle, the cleaning cycle, the calibration, the air flow rate, the liquid entry, and the opening and closing of the drain line 36.

In operation, the receptacle 12 is installed in a suitable location within the area that is being monitored for the presence of chemical vapors. For example, in the case of explosives, the receptacle 12 will be installed in a ventilating duct of a building such as a transportation terminal (airport, train station, bus station, etc.) or a courthouse, post office, auditorium or other building that is being monitored.

The device 10 can be operated in either a semiautomatic or manual mode of operation. In the semiautomatic mode, the programmable controller 68 is programmed to effect sequential operating cycles. In the manual mode, the switches 76 may be hand operated to carry out the various functions that are performed during each cycle.

Each cycle of sample collection is initiated by opening the liquid valve 28 long enough to introduce the desired amount of scrubbing liquid into the receptacle 12 through the inlet lines 24. Normally, the volume of liquid that is used during each operating cycle is in the range of about 3.5 to 4.5 milliliters, although other volumes can be used. When the desired amount of liquid has entered the receptacle, the valve 28 is closed.

Then, the vacuum pump 54 is energized to apply vacuum to the vacuum line 52 and thus to the interior of the receptacle 12 near its top end 16. The application of vacuum draws ambient air into the receptacle 12 through the inlet slit 40, and the air is pulled into the receptacle tangentially to the wall 14, as indicated by the directional arrows 44 in FIG. 3. The tangential flow of air effects a swirling pattern of air inside of the receptacle, as indicated by the directional arrows 78 in FIG. 2. The air thus swirls in a spiral pattern within the receptacle 12 from the inlet slit 40 toward the outlet ports 50. The air that is drawn into the receptacle makes contact with the scrubbing liquid and thus causes the liquid to spin such that it is carried in a swirling motion with the air. Thus, the liquid essentially coats the entirety of the inside surfaces of the wall 14, the funnel 30, and the cone 46. Consequently, as the air swirls through the receptacle 12, it is scrubbed by the liquid which coats the inside surfaces of the receptacle, and any chemical vapor that is contained in the air is scrubbed by the liquid.

Normally, the air flow rate is in the range of approximately 100 to 235 liters per minute, and an operating cycle is typically about 15 minutes long. At the end of the cycle, the vacuum pump 54 is deenergized to interrupt the air flow through the receptacle. The scrubbing liquid and the chemical vapor that has been scrubbed by it then settle to the bottom of the receptacle, and the solenoid valve 38 is opened to drain the liquid and chemical vapor to a suitable system which analyzes the chemical content in the liquid. When all of the liquid has been drained, the solenoid valve 38 shuts, thus closing the drain line 36.

Before the next sampling cycle takes place, the heater cable 56 is energized to heat the receptacle 12 to a temperature of approximately 250° Celsius. This takes place in a cleaning cycle during which the interior of the receptacle is cleaned. Raising the receptacle temperature to this high level enhances the cleaning effect and the removal of foreign material. Preferably, the receptacle 12 is constructed of stainless steel so that it can better withstand the heat.

When the cleaning cycle has been completed, another sampling cycle can be carried out, again either semiautomatically under control of the programmable controller 68 or manually by an operator activating the proper switches in the bank of switches 76. In practice, the cleaning cycle need only be carried out after a positive determination of the presence of chemicals has been indicated by a suitable analyzer, rather than after every sampling cycle. It is contemplated that a calibration routine will be carried out at regular intervals, e.g., once a week, in order to confirm that the device is performing satisfactorily.

Because of the relatively high volume of air flow through the device during each sample collection cycle, any chemical vapor that is contained in the air will be concentrated in the liquid scrubbing medium to a high enough level that it can be detected by known analyzing techniques. In addition, by reason of the geometry of the device and the pattern of flow through it, the air samples are thoroughly scrubbed by the scrubbing liquid so that the concentration of, for example, the explosives vapor is enhanced, thereby improving detection of explosives vapor indicative of the presence of a bomb or other explosive device.

From the foregoing, it will be seen that this invention is well adapted to attain all the ends and objectives hereinabove set forth together with other advantages which are obvious and inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not limiting.

Specifically, the invention has utility for sampling of chemical vapors beyond explosives. These include pesticides, herbicides, nerve gases, street drugs, tobacco smoke, etc. Therefore, it is considered that a general chemical vapor sampler has been invented and further developed and tested with explosives vapor.

Having thus described the invention, we claim:

1. A method of extracting chemical vapor from air and concentrating the extracted vapor, said method comprising the steps of:
   delivering a preselected quantity of scrubbing liquid to an enclosed receptacle having a substantially cylindrical wall;
   introducing air into the receptacle tangentially to said wall to effect swirling of the air and carrying of the liquid therewith along the wall so that the liquid scrubs the air of chemical vapor therein;
   terminating the introduction of air into the receptacle after a preselected time to permit the liquid with chemical vapor therein to settle in the receptacle; and
   draining the liquid with the chemical vapor therein from the receptacle.

2. A method as set forth in claim 1, including the step of heating said receptacle after draining of the liquid with the chemical vapor therein.

3. Apparatus for extracting chemical vapors from air and concentrating the vapors for analysis, said apparatus comprising:
   a hollow receptacle having a substantially cylindrical wall and an air inlet slit in said wall for admitting air to the receptacle tangentially to said wall, said receptacle having an air outlet spaced from said inlet slit;
   a liquid inlet port for introducing a scrubbing liquid to said receptacle;
   means for effecting air flow into said inlet slit and out through said outlet to swirl the air along the wall of the receptacle and carry the liquid with the air such that the liquid coats the wall for scrubbing the air of chemical vapor therein;
   a drain port in said receptacle for draining liquid and chemical vapor therein from the receptacle;
   valve means for opening and closing said drain port; and
   means for terminating the air flow through the receptacle and then operating said valve means to open the drain port after the liquid and chemical vapor therein has settled in the receptacle.

4. Apparatus as set forth in claim 3, including means for heating the receptacle after the liquid and chemical vapor have been drained from the receptacle through said drain port.

5. Apparatus for extracting chemical vapor from ambient air and concentrating the vapor for analysis, said apparatus comprising:
   a hollow receptacle having top and bottom ends and a substantially cylindrical wall, said wall having an air inlet slit for admitting air to the receptacle in a direction substantially tangential to said wall;
   means for applying vacuum to the interior of said receptacle to draw air through said inlet slit and through the receptacle in a swirling pattern;
   a liquid supply line extending to said receptacle to deliver scrubbing liquid thereto;
   means for supplying a preselected quantity of liquid through said supply line to the interior of said receptacle in a manner to effect swirling of the liquid with the air to coat said wall with the liquid so that the liquid scrubs the air of chemical vapor therein;
   a drain line extending from the bottom end of said receptacle for draining the liquid and chemical vapor therein from the receptacle when the drain line is open and said vacuum applying means is deenergized;
   valve means for selectively opening and closing said drain line; and
   heating means for heating said receptacle after the liquid and chemical vapor therein have been drained from the receptacle through said drain line.

* * * * *